United States Patent [19]

Rabenau et al.

[11] Patent Number: 4,943,704
[45] Date of Patent: Jul. 24, 1990

[54] HUMIDIFIER APPARATUS

[75] Inventors: Richard Rabenau, Arab; Rowland W. Kanner; Joseph J. Cerola, both of Guntersville, all of Ala.

[73] Assignee: Ryder International Corporation, Arab, Ala.

[21] Appl. No.: 307,261

[22] Filed: Feb. 6, 1989

[51] Int. Cl.⁵ .............................................. F22B 1/28
[52] U.S. Cl. .................................... 219/275; 261/142; 261/104; 261/79.2; 219/273
[58] Field of Search ................................ 219/271–276, 219/362; 261/142, 104, 79.2

[56] References Cited

U.S. PATENT DOCUMENTS

| | | | |
|---|---|---|---|
| 1,323,181 | 11/1919 | Goodfellow | 261/142 |
| 2,850,615 | 9/1958 | Luse | 219/271 |
| 3,584,193 | 6/1971 | Badertscher | 219/275 |
| 4,028,526 | 6/1977 | Schossow | 219/272 |
| 4,532,088 | 7/1985 | Miller | 261/142 |
| 4,657,713 | 4/1987 | Miller | 261/142 |
| 4,753,758 | 6/1988 | Miller | 261/139 |

OTHER PUBLICATIONS

Product Literature and Operator's Manual for Vapor-Phase ® Models of Intertech Resource, Inc.

*Primary Examiner*—Teresa J. Walberg
*Attorney, Agent, or Firm*—R. A. Giangiorgi

[57] ABSTRACT

A humidifier apparatus for admixture of heated water vapor into a gaseous stream include heating means for generating heated vapor from the water and a housing with a transfer chamber formed therein secured to the heating means which is exposed within the chamber. The housing includes intake and effluent conduit for flow passage of the gaseous stream through the chamber and a water intake conduit extending through the housing and chambers so that the conduit directs discharge of the intake water against the heating means to generate the heated vapor.

34 Claims, 3 Drawing Sheets

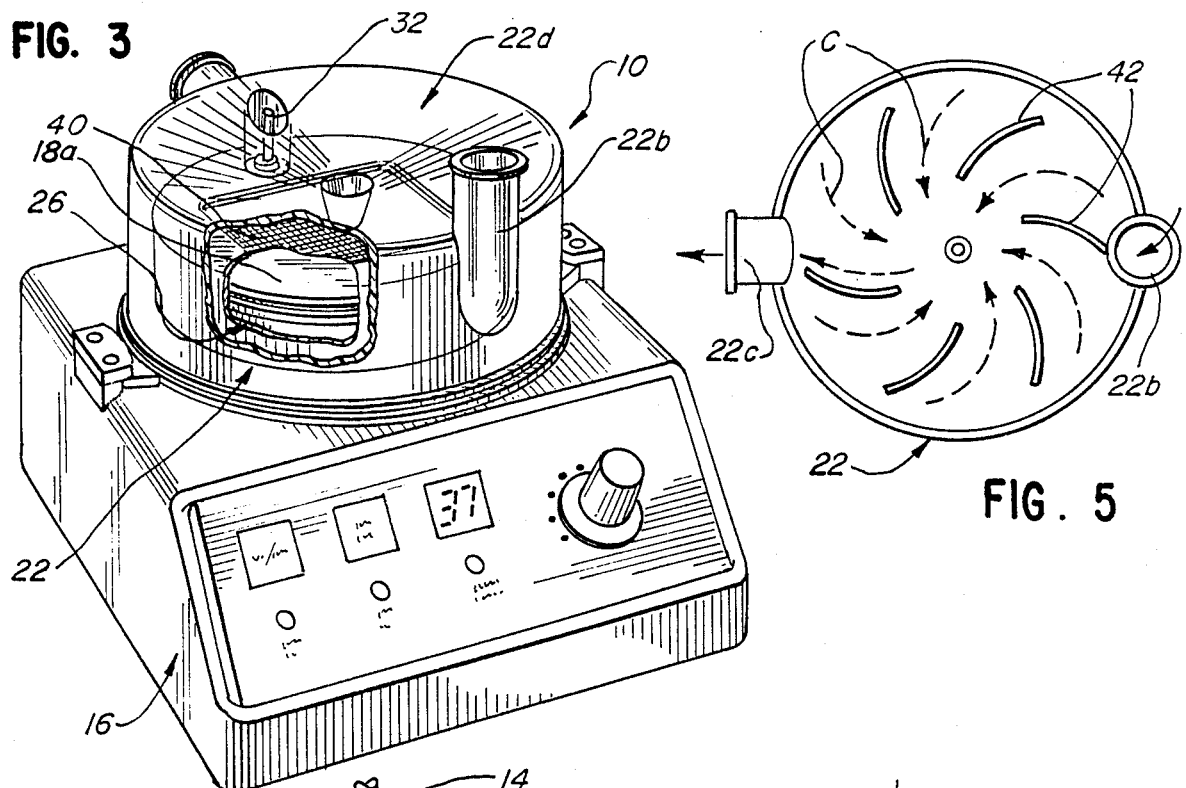
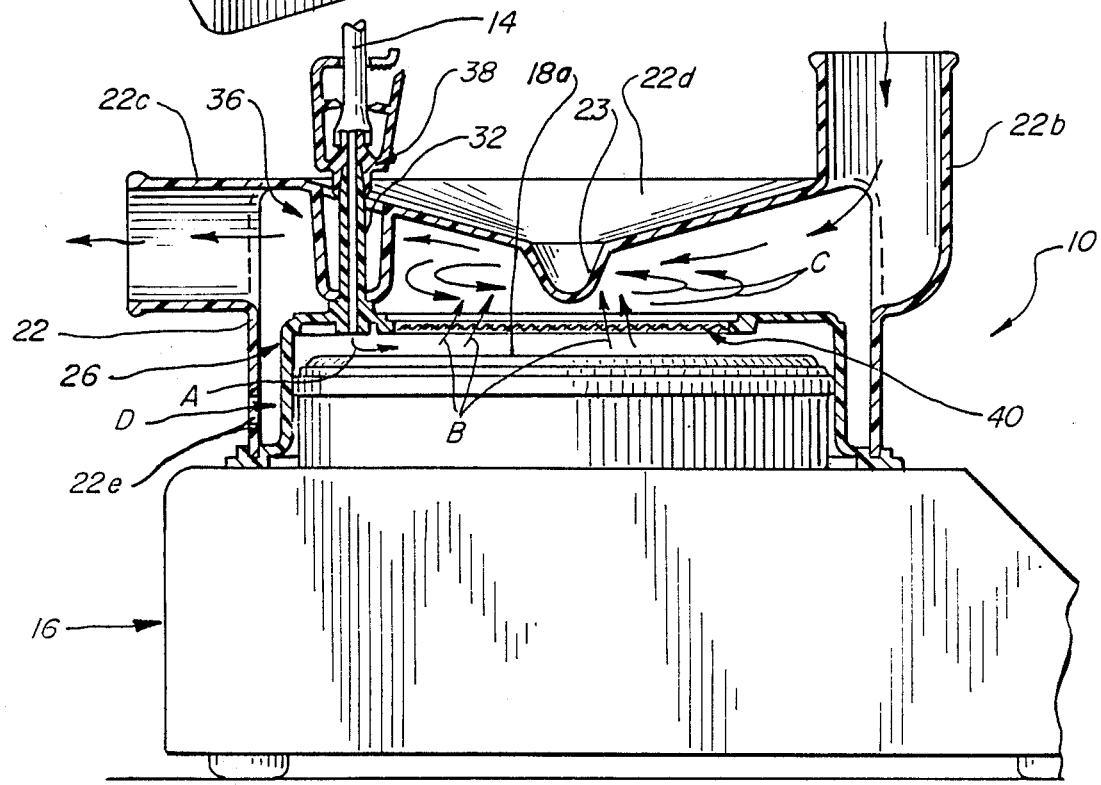
FIG. 3
FIG. 5
FIG. 4

4,943,704

HUMIDIFIER APPARATUS

BACKGROUND OF THE INVENTION

This application relates to apparatus for humidifying a gaseous stream such as air or oxygen, more particularly, relates to apparatus for admixture of water vapor into such a stream, particularly for use in medical applications such as anesthesia, inhalation therapy, and neonatal and pediatric service.

Medical application humidifiers which provide warm humidified breathing gas have been developed for pressure-cycled and volume-controlled patient ventilators as well as for continuous flow operation, such as the Vapor-Phase instruments commercially available from Intertech Resources, Inc. These humidifier instruments employ a heating element to heat a water supply which generates water vapor thereafter passed through a vapor permeable membrane into a separate ventilation stream of air or oxygen directed through the instrument for delivery to the patient.

Conventionally, the gaseous stream is directed through a reservoir chamber disposed above the heating element which drives the water vapor through the membrane upwardly into the gaseous stream passing above through the chamber. While such instruments have proved successful, a recurring tendency for vapor condensation to accumulate in the upper chamber occasionally result in water droplets entrained in gaseous stream which can later settle to form an obstruction downstream from the humidifier instrument. Furthermore, there has been no on-line provision for drainage of the condensate. Additionally, the water supply inlet in the base structure delivers the water to a check valve which controls the passage into contact with the heating element, and the check valve itself represents a water leakage hazard in proximity to the electrical circuitry which powers the heating element.

These disadvantages are eliminated by the the improved humidifier apparatus according to the present invention.

SUMMARY OF THE INVENTION

In accordance with the present invention, a humidifier apparatus for admixture of heated water vapor into a gaseous stream includes heating means for generating heated vapor from the water and a housing with a transfer chamber formed therein secured to the heating means which is exposed within the chamber. The housing includes intake and effluent conduits for flow passage of the gaseous stream through the chamber and a water intake conduit extending through the housing and chamber so that the conduit directs discharge of the intake water against the heating means to generate the heated vapor.

In one embodiment, the housing includes a generally dome-shaped cover overlying a hydrophobic filter element secured in a support structure for passage of the heated water vapor into the gaseous stream, and the water intake conduit passes through both the cover and the support structure so that it is separated from proximity to the electrical circuitry supplying power to a heating platen. The intake water is discharged against the platen to generate the heated water vapor which selectively passes through the hydrophobic filter into the gaseous stream. The hydrophobic filter is centrally supported within the support structure and the water intake conduit passes through the cover and the support structure at a location generally offset in relation to the central filter. The housing cover has a generally concave, conical wall and central baffle which compress and direct the gaseous flow in a generally centrally swirling pattern to promote the retention and residence time of the gaseous stream within the chamber to enable increased humidification by the admixture of the heated water vapor passing through the filter. The conical wall of the cover also increases the velocity of the gaseous stream which retards water vapor condensation within the chamber. Any condensation which does accumulate is drained from the cover through a drainage port therein.

In another embodiment the humidifier apparatus is provided with a water supply pouch or container in which the hydrophobic filter is integrated with a heat-conducting wall of the pouch which is seated on the heating platen so that heat is conducted through the heat conducting wall of the pouch to generate water vapor therein. The water vapor passes from the pouch through the hydrophobic filter into the gaseous stream. The pouch is coupled to a water intake conduit which passes through the housing and chamber and is separated from proximity to the electrical circuitry which supplies power to the heating platen.

BRIEF DESCRIPTION OF THE DRAWINGS

FIG. 3 is a perspective view of the assembled humidifier apparatus as shown in FIG. 1, partially broken away to illustrate internal structure thereof;

FIG. 4 is a vertical, cross-sectional view of the humidifier apparatus shown in FIG. 3;

FIG. 5 is a diagrammatic plan view showing the swirling flow pattern of the gaseous stream passing through the humidifier apparatus in the manner similar to the flow path shown in FIG. 4;

DETAILED DESCRIPTION OF THE ILLUSTRATED EMBODIMENT

Figure 1:
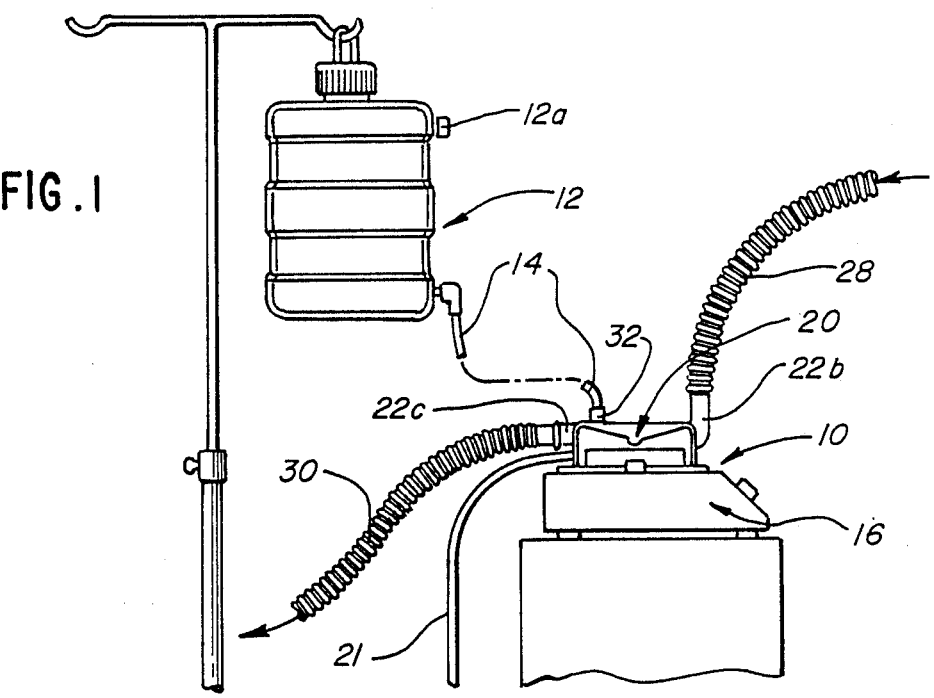
FIG. 1 is an elevation view of the ventilating system including one embodiment of the humidifier apparatus in accordance with the present invention.
Figure 2:
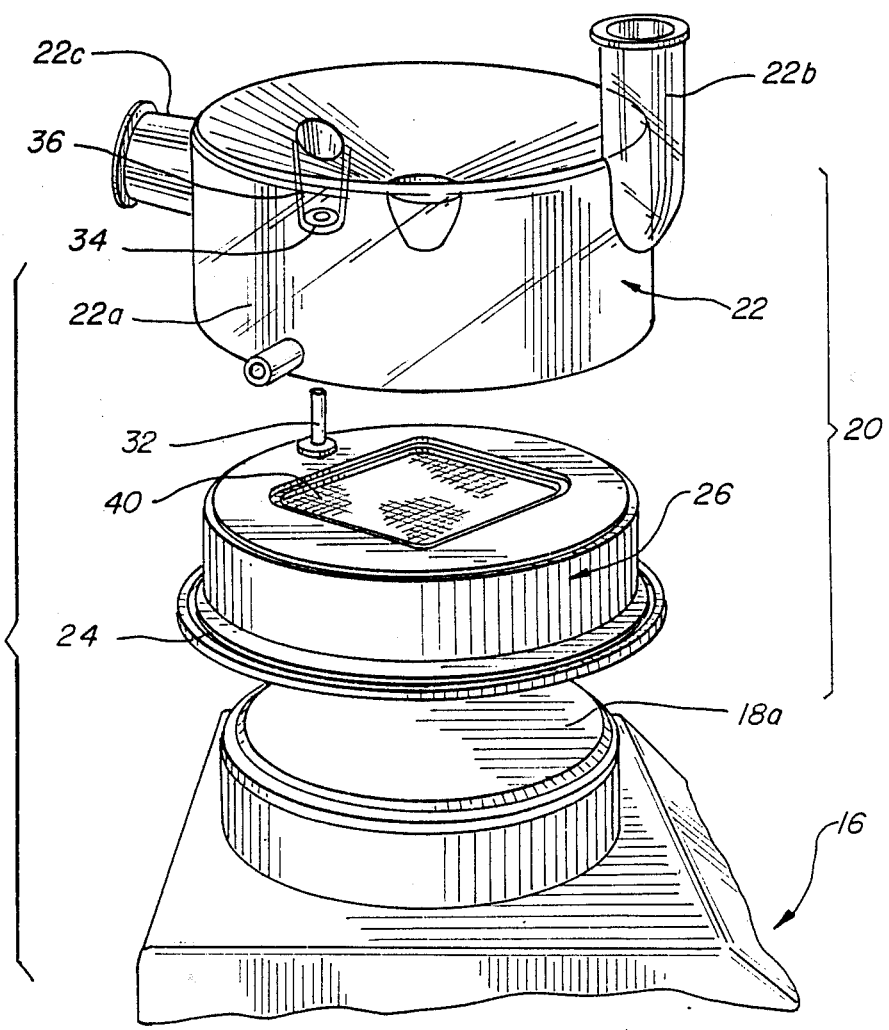
FIG. 2 is an exploded, perspective view of the humidifier apparatus shown in FIG. 1.

Referring to FIG. 1, an embodiment of the humidifier apparatus of the invention is generally designated by reference character 10 and is shown with a water supply reservoir 12 from which water is delivered to the humidifier apparatus to a supply tube 14. The reservoir 12 is provided with a filtered air vent 12a to prevent air-borne microbial contamination of the water supply within the reservoir. The humidifier apparatus 10 includes a base generally designated by reference character 16 which houses conventional operation and control circuitry (not shown) and supports an upwardly projecting heater element 18 having a generally planar heating surface or platen 18a as shown in FIG. 2. The humidifier apparatus 10 further includes a vapor transfer chamber 20 which is seated on the base 16 and generally forms an upper, overlying enclosure upon the heating element 18. As shown in FIG. 2, the chamber 20 has a disposable, two part construction in which an upper dome-shaped cover member 22 overlies and seats on an annular seating flange 24 radially projecting and integrally molded with an inner, filter support structure generally designated by a reference character 26.

Referring again to FIG. 1, the cover 22 includes an upstanding annular wall 22a provided with a gas intake nipple and port 22b connected to an intake hose 28 for the gaseous stream to be humidified in the apparatus 10, such as ventilating air, oxygen, or vapor phase anesthetic. The wall 22a also has a gas discharge nipple on port 22c arranged diametrically opposing the nipple 22b in order to extend residence time of the gaseous stream within the chamber 20 to promote the humidifying admixture of heated water vapor transfer into the gaseous stream which is discharged through the nipple 22c into the discharge tube 30.

The water supply tube 14 is coupled to a generally rigid and upstanding tube 32 which is preferably integrally molded with the support 26. The tube 32 passes through an annular boss 34 formed at the bottom of an internal cylindrical wall 36 integrally formed in the cover 22 to provide protective passageway for the tube 32 through the dome 22 as best shown in FIG. 3. The tube 32 and boss 34 are located offset from the center of the cover 22 and support 26 as best shown in FIG. 4.

Referring particularly to FIG. 4, a unitary tubing connector and pinch valve 34 can be mounted on the upper end of the tube 32 for coupling and control of water supply through the tube 14 into the humidifier apparatus 10. From the tube 32, the supply water is directed through the support 26 and delivered into contact with the exposed surface of the heating platen 18a as indicated by the arrow A. The delivered water is heated and vaporized by the heating platen 18 and the resulting distilled water vapor rises as indicated by the arrows B and passes through the hydrophobic filter membrane generally designated by reference character 40 which is centrally located and supported by the support structure 26 so that the filter is oriented parallel to the planar heating platen surface. The hydrophobic filter 40 allows passage of the sterile, heated water vapor but obstructs liquid water potentially containing microbial or other contaminents. A conventional hydrophobic filter membrane, fabricated for example, from Gore-Tex ® in suitable pore size of approximately 0.2 micron, can thus be mounted centrally within the support structure 26 as a continuous expanse without interruption by reinforcement ribs or the like since the tube 32 is offset and does not pass through the filter 40, water is constantly replenished from the reservoir 12.

The sterile heated water vapor passes through the filter 40 and is then admixed to humidify the gaseous stream flowing from the inlet port 22b to the outlet port 22c for delivery to the ventilated patient.

In order to increase the residence time of the gaseous stream within the chamber 20 and thereby promote increase in the level of transferred water vapor and resulting humidification of the gaseous stream, the cover 22 has a concave or conical upper wall 22d which inclines downwardly to a generally centrally located baffle formation 23. The baffle 23 has a generally smoothly curved and further downwardly projecting bell-shaped configuration which cooperates with the conical wall 22d to compress and direct the inlet gaseous stream into a generally centrally swirling flow pattern (as indicated by arrows C) which lengthens the retention or residence time of the stream within the chamber 22 prior to discharge. As shown in FIG. 5, the swirling pattern of the stream can be further promoted by providing additional swirl-directing vanes 42 which can be downwardly projecting from and integrally molded with the conical wall 22d of the cover 22 in various suitable vane patterns. The compression and swirling of the gaseous stream increases the velocity of the stream which not only promotes increased admixture of the humidifying water to the stream, but also retards any tendency for water vapor condensation on the inner surface of the chamber 20.

Any water vapor condensate which may condense within the chamber 22 will be accumulated within the annular clearance space D formed between the respective upstanding walls of the inner support 26 and the cover 22; the condensate can be conveniently drained through the drain port 22e which is coupled to a drain tube 21 shown in FIG. 1 so that the drained condensate prevents liquid water entrainment in the gaseous stream.

Figure 6:
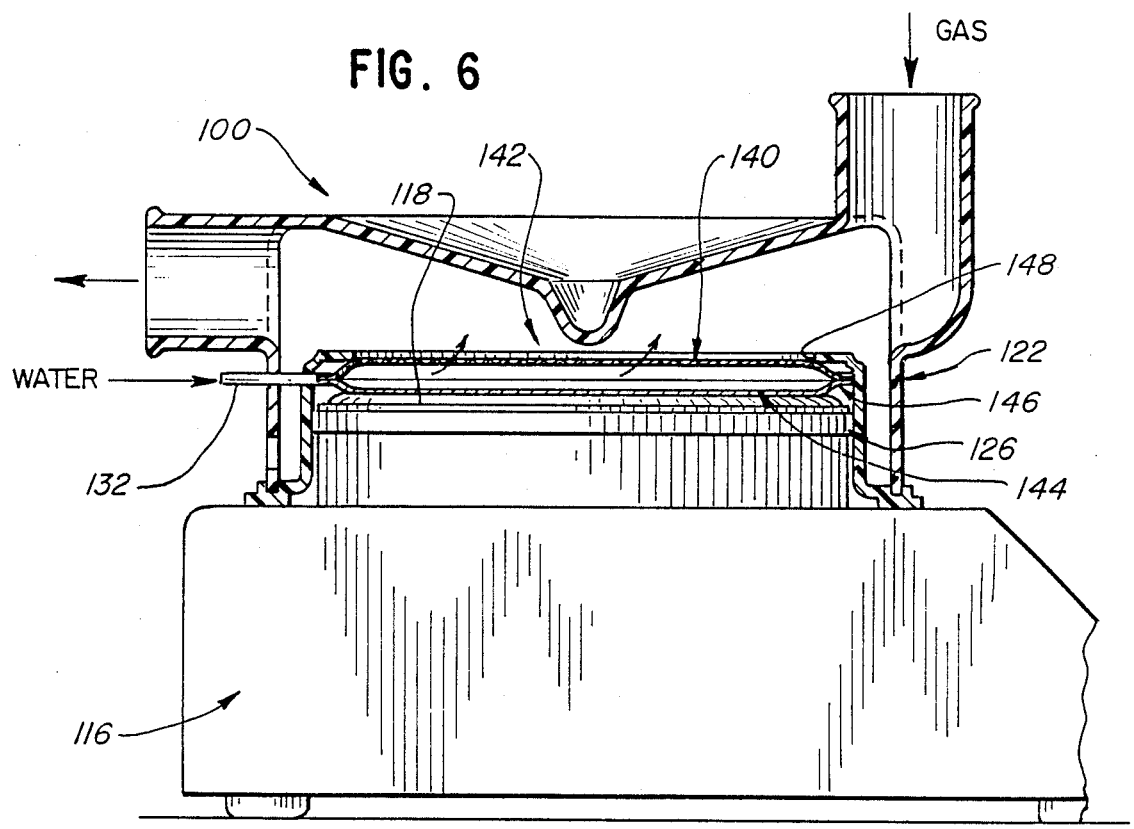
FIG. 6 is a vertical, cross-sectional view of a second embodiment of the humidifier apparatus in accordance with the present invention.
Figure 7:
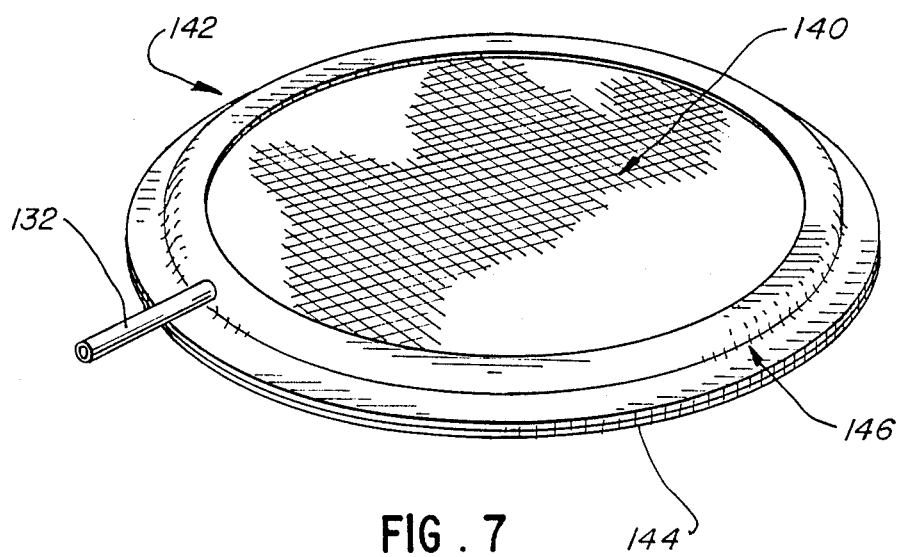
FIG. 7 is a perspective view of a water delivery and reservoir pouch with integrally formed membrane for vapor passage, as shown in FIG. 6.

Referring now to FIGS. 6 and 7, a second embodiment of the humidifier apparatus of the invention is generally designated by reference character 100 which is similar to the apparatus 10 in FIG. 4 with the exception that in the apparatus 100, the hydrophobic water vapor filter 140 is integrated with a water supply intake tube 132 to form a unitary water pouch 142. The upper horizontal wall of the pouch 142 is formed by the filter 140 while the lower horizontal wall 144 is a generally thin sheet or film of heat conducting material, for example, a metallic foil which is seated upon the heated platen surface 118 and through which the heat is conducted to generate water vapor from the water supplied into the pouch 142. The filter 140 and the heat-conducting wall 144 are circumferentially joined by an annular rim 146 which can be either rigid or flexible material since the water enclosed within the pouch supports the filter 140 and provides structural integrity for the pouch. The filter 140 is positioned so that it is concentric with a large aperture 148 formed in the upper horizontal wall of the inner, transfer chamber support member 126. In the embodiment shown in FIG. 6, the water inlet tube passes laterally through both of the respective upstanding walls of the inner support 126 and the cover member 122 in a manner similar to the first embodiment of the vapor transfer chamber 20.

The pouch 142 can be inexpensively fabricated so that it will be disposable with the vapor transfer chamber formed by the support 126 and the cover member 122.

In operation, the water supplied through the tube 132 into the pouch 142 is heated by the platen 118 and conducting wall 144 so that the resulting sterile heated water vapor passes through the filter 140 into the swirling gaseous stream (not shown) which is directed through cover member 122 in the manner similar to the humidification shown in FIG. 4. As shown in FIG. 6, the water supply through tube 132 into the pouch 142 is again isolated from the electrical circuitry (not shown) which is contained within the base 116 for supplying power to heat the platen 118. Additionally, the pouch 142 and wall 144 separate the water from direct contact with the platen 118 so that any build-up of mineral deposits or other residue from the water supply is retained on the interior surface of the disposable wall 144 and pouch 142, thus preventing water residue and fouling of the platen in continuous humidification service.

In light of the foregoing description of the embodied humidifier apparatus, it will be evident to those skilled in design of such humidifiers that various aspects may be modified without departing from the invention. As such, the scope of the invention is not limited by the particular embodiment illustrated and described herein and is defined by the appended claims and equivalents thereof.

The invention is claimed as follows:

1. A humidifier apparatus for admixture of heated water vapor into a gaseous stream, comprising:
   (a) a heating structure including a heating means for generating heated vapor from water;
   (b) an upper housing and chamber having a flow passageway for said gaseous stream formed in said housing secured to said heating structure and within which said heating means is exposed, including:
      (1) intake and effluent conduits for flow passage of said gaseous stream through said chamber flow passageway; and
      (2) a water intake conduit extending through said housing and entirely through said chamber flow passageway, and directing discharge of said water against said heating means.

2. A humidifier apparatus according to claim 1 wherein said upper housing includes a generally dome-shaped cover member overlying a hydrophobic filter means secured in a support structure for passage of said heated water vapor through said filter means into said gaseous stream.

3. A humidifier apparatus according to claim 2 wherein said water intake conduit passes through both said cover and said support structure.

4. A humidifier apparatus according to claim 3 wherein said hydrophobic filter means is centrally supported within said support structure, and wherein said passage of said water intake conduit through said cover and support structure is spaced from said filter means in offset relation thereto.

5. A humidifier apparatus according to claim 2 wherein said cover member comprises an overlying, upper wall having a generally concave configuration in order to promote compression of said gaseous stream flow through said chamber.

6. A humidifier apparatus according to claim 5 wherein said concave configuration is defined by a conical inclination of said wall downwardly toward a generally central apex.

7. A humidifier apparatus according to claim 6 wherein a downwardly projecting baffle means is formed at said generally central apex in order to promote generally circulating flow of said gaseous stream within said chamber for extension of residence time and resulting humidification thereof.

8. A humidifier apparatus according to claim 6 wherein said conical wall includes at least one downwardly projecting vane means for guiding circulation of said gaseous steam within said chamber.

9. A humidifier apparatus according to claim 2 wherein said cover member includes a drainage port for drainage of any accumulated water vapor condensate formed within said chamber.

10. A housing and transfer chamber for a humidifier apparatus producing admixture of heated water vapor into a gaseous stream, comprising: a transfer chamber including a flow passageway for said gaseous stream, formed within a generally disposable upper housing for removable securement to a base having a heating element to generate said heated water vapor, said housing including intake and effluent conduits for flow passage of said gaseous stream through said chamber flow passageway, and a water intake conduit extending through said housing and chamber for directing discharge of intake water against said heating element in order to generate said admixed water vapor.

11. A housing and transfer chamber according to claim 10 wherein said upper housing includes a generally dome-shaped cover member overlying a hydrophobic filter means secured in a support structure for passage of said heated water vapor through said filter means into said gaseous stream.

12. A housing and transfer chamber according to claim 11 wherein said water intake conduit passes through both said cover member and said support structure.

13. A housing and transfer chamber according to claim 12 wherein said hydrophobic filter means is centrally supported within said support structure, and wherein said passage of said water intake conduit through said cover member and support structure is spaced from said filter means in offset relation thereto.

14. A housing and transfer chamber according to claim 11 wherein said cover member comprises an overlying, upper wall having a generally concave configuration in order to promote compression of said gaseous stream flow through said chamber.

15. A housing and transfer chamber according to claim 14 wherein said concave configuration is defined by a conical inclination of said wall downwardly toward a generally central apex.

16. A housing and transfer chamber according to claim 15 wherein a downwardly projecting baffle means is formed at said generally central apex in order to promote generally circulating flow of said gaseous stream within said chamber for extension of residence time and resulting humidification thereof.

17. A housing and transfer chamber according to claim 11 wherein said cover member has a conical wall which includes at least one vane means for guiding circulation of said gaseous stream within said chamber.

18. A housing and transfer chamber apparatus according to claim 10 wherein said housing includes a drainage port for drainage of any accumulated water vapor condensate formed within said chamber.

19. A housing and transfer chamber for a humidifier apparatus producing admixture of heated water vapor into a gaseous stream, comprising: a transfer chamber formed within a generally disposable upper housing for removable securement to a base having a heating element to generate said heated water vapor, and a unitary, water container structure comprising a heat-conducting wall for heat-conducting engagement against said heating element in order to generate water vapor from said water within said water container structure, and a hydrophobic filter means integrally secured to form a second wall of said water container structure, said filter means providing selective passage therethrough for water vapor generated from water within said water container structure in order to provide said water vapor admixture into said gaseous stream, said housing further including intake and effluent conduits for flow passage of said gaseous stream through said chamber.

20. A housing and transfer chamber according to claim 19 further comprising a water intake conduit extending through said housing and chamber and coupled to said water container structure for water supply thereinto.

21. A housing and transfer chamber as claimed in claim 19 wherein said filter means and said heat-conducting wall are peripherally joined by a rim structure.

22. A unitary water container structure for installation within a transfer chamber of a humidifier apparatus which produces an admixture of heated water vapor into a gaseous stream, in which the transfer chamber is formed within a generally disposable upper housing for removable securement to a base of the humidifier apparatus having a heating element to generate the heated water vapor, said water container structure comprising: a heat-conducting wall for heat-conducting engagement against said heating element in order to generate water vapor from water within said water container structure, and a hydrophobic filter means integrally secured to form a second wall of said water container structure, said filter means providing selective passage therethrough for water vapor generated from water within said water container structure, in order to provide said water vapor admixture into said gaseous stream.

23. A water container structure according to claim 22 further comprising an integral water intake conduit for extension through said housing and chamber.

24. A water container structure according to claim 22 wherein said filter means and said heat-conducting wall are peripherally joined by a rim structure.

25. A humidifier apparatus for admixture of heated water vapor into a gaseous stream, comprising:
  (a) a heating structure including a heating means for generating heated vapor from water;
  (b) an upper housing including a generally dome-shaped cover member and chamber formed in said housing secured to said heating mixture and within which said heating means is exposed, said cover member overlying a hydrophobic filter means secured in a support structure for passage of said heated water vapor through said filter means into said gaseous stream, said upper housing further including:
    (1) intake and effluent conduits for flow passage of said gaseous stream through said chamber; and
    (2) a water intake conduit extending through said cover member and said support structure, wherein said passage of said water intake conduit through said cover and support structure is spaced from said filter means in offset relation thereto.

26. A humidifier apparatus for admixture of heated water vapor into a gaseous stream, comprising:
  (a) a heating structure including a heating means for generating heated vapor from water;
  (b) an upper housing including a generally dome-shaped cover member overlying a hydrophobic filter means secured in a support structure for passage of said heated water vapor through said filter means into said gaseous stream, said cover member having a chamber formed therein and comprising an overlying, upper wall having a generally concave configuration in order to promote compression of said gaseous stream flow through said chamber, and within which said heating means is exposed, said housing being secured to said heating structure and further including intake and effluent conduits for flow passage of said gaseous stream through said chamber; and
  (c) a water intake conduit extending through said housing and chamber and directing discharge of said water against said heating means.

27. A humidifier apparatus according to claim 26 wherein said concave configuration is defined by a conical inclination of said wall downwardly toward a generally central apex.

28. A humidifier apparatus according to claim 27 wherein a downwardly projecting baffle means is formed at said generally central apex in order to promote generally circulating flow of said gaseous stream within said chamber for extension of residence time and resulting humidification thereof.

29. A humidifier apparatus according to claim 26 wherein said concave wall includes at least one downwardly projecting vane means for guiding circulation of said gaseous stream within said chamber.

30. A housing and transfer chamber for a humidifier apparatus producing admixture of heated water vapor into a gaseous stream, comprising:
  (a) a transfer chamber formed within a generally disposable upper housing for removable securement to a base having a heating element to generate said heated water vapor, said upper housing including a generally dome-shaped cover member overlying a hydrophobic filter means secured in a support structure for passage of said heated water vapor through said filter means into said gaseous stream;
  (b) said housing further including intake and effluent conduits for flow passage of said gaseous stream through said chamber; and
  (c) a water intake conduit extending through said cover member and support structure, and spaced from said filter means in offset relation thereto, for directing discharge of intake water against said heating element in order to generate said admixed water vapor.

31. A housing and transfer chamber for a humidifier apparatus producing admixture of heated water vapor into a gaseous stream, comprising:
  (a) a transfer chamber formed within a generally disposable upper housing for removable securement to a base having a heating element to generate said heated water vapor, said housing including said intake and effluent conduits for flow passage of said gaseous stream through said chamber;
  (b) and a water intake conduit extending through said housing and chamber for directing discharge of intake water against said heating element in order to generate said admixed water vapor;
  (c) said upper housing including a generally dome-shaped cover member overlying a hydrophobic filter means secured in a support structure for passage of said heated water vapor through said filter means into said gaseous stream and wherein said cover member comprises an overlying, upper wall having a generally concave configuration in order to promote compression of said gaseous stream flow through said chamber.

32. A humidifier apparatus according to claim 31 wherein said concave configuration is defined by a conical inclination of said wall downwardly toward a generally central apex.

33. A humidifier apparatus according to claim 32 wherein a downwardly projecting baffle means is formed at said generally central apex in order to promote generally circulating flow of said gaseous stream within said chamber for extension of residence time and resulting humidification thereof.

34. A humidifier apparatus according to claim 31 wherein said concave configuration includes at least one downwardly projecting vane means for guiding circulation of said gaseous stream within said chamber.

* * * * *